(12) United States Patent
Nies et al.

(10) Patent No.: US 8,974,541 B2
(45) Date of Patent: Mar. 10, 2015

(54) BONE IMPLANT COMPRISING A MAGNESIUM-CONTAINING METALLIC MATERIAL WITH REDUCED CORROSION RATE, AND METHODS AND KIT FOR PRODUCING THE BONE IMPLANT

(75) Inventors: Berthold Nies, Fränkisch-Crumbach (DE); Stefan Glorius, Constance (DE)

(73) Assignee: InnoTERE GmbH, Radebeul (DE)

( * ) Notice: Subject to any disclaimer, the term of this patent is extended or adjusted under 35 U.S.C. 154(b) by 170 days.

(21) Appl. No.: 13/704,346
(22) PCT Filed: Jun. 15, 2011
(86) PCT No.: PCT/EP2011/059954
  § 371 (c)(1),
  (2), (4) Date: Mar. 2, 2013
(87) PCT Pub. No.: WO2011/157758
  PCT Pub. Date: Dec. 22, 2011

(65) Prior Publication Data
  US 2013/0150978 A1    Jun. 13, 2013

(30) Foreign Application Priority Data
  Jun. 15, 2010 (DE) .......................... 10 2010 030 135

(51) Int. Cl.
  *A61F 2/28* (2006.01)
  *A61L 24/02* (2006.01)
  (Continued)
(52) U.S. Cl.
  CPC . *A61F 2/28* (2013.01); *A61L 24/02* (2013.01); *A61L 27/047* (2013.01);
  (Continued)
(58) Field of Classification Search
  CPC .................. A61F 2/28; A61F 2/2846; A61F 2/30723–2/30767; A61F 2002/28; A61F 2002/2817; A61F 2002/2835–2002/285; A61F 2002/30011; A61F 2002/30028; A61F 2002/3006; A61F 2002/30062; A61F 2002/30064; A61F 2002/30107; A61L 24/02; A61L 2430/02
  USPC .......... 623/11.11, 16.11, 17.11, 17.16, 18.11, 623/23.48–23.62, 23.72–23.76; 606/60, 606/246–249, 62, 65, 67, 907–909; 427/2.26, 2.27
  See application file for complete search history.

(56) References Cited

U.S. PATENT DOCUMENTS 3,964,470 A * 6/1976 Trombley ...................... 600/377
4,705,561 A * 11/1987 Green ............................. 75/315
(Continued)

FOREIGN PATENT DOCUMENTS

DE        101 63 106 A1    7/2003
DE    10 2006 060 501 A1    6/2008
(Continued)

*Primary Examiner* — Alvin Stewart
(74) *Attorney, Agent, or Firm* — Gudrun E. Huckett (57) ABSTRACT

The invention relates to a bone implant which comprises a magnesium-containing metallic material having a reduced corrosion rate and inorganic bone cement, and to methods and a kit for producing the bone implant. With a method according to the invention, it is possible to obtain a bone implant which comprises inorganic bone cement and a magnesium-containing metallic material with a corrosion-inhibiting coating which contains magnesium-ammonium phosphates. In the method according to the invention, a magnesium-containing metallic material, of which the surface has a magnesium oxide layer and/or a magnesium salt layer, is combined with inorganic bone cement in order to generate a solid composite material that comprises the inorganic bone cement and the magnesium-containing metallic material. The inorganic bone cement contains inorganic powder constituents, which set in the presence of water to form a solid, and water-soluble phosphate-ion-containing salts, preferably water-soluble phosphate-ion-containing and ammonium-ion-containing salts. According to the invention, the magnesium-containing metallic material is brought into contact with water before and/or during the combination with the inorganic bone cement in the presence of water-soluble ammonium-ion-containing and phosphate-ion-containing salts. Moreover, the inorganic bone cement is set by being brought into contact with water.

16 Claims, 4 Drawing Sheets

(51) Int. Cl.
*A61L 27/04* (2006.01)
*A61L 27/30* (2006.01)

(52) U.S. Cl.
CPC .......... *A61L 27/306* (2013.01); *A61L 2430/02* (2013.01)
USPC ...................................................... 623/23.6

(56) References Cited

U.S. PATENT DOCUMENTS

| | | | |
|---|---|---|---|
| 5,164,187 A * | 11/1992 | Constantz et al. ............ 424/423 |
| 5,788,687 A * | 8/1998 | Batich et al. ................ 604/890.1 |
| 6,207,218 B1 * | 3/2001 | Layrolle et al. .............. 427/2.27 |
| 6,306,422 B1 * | 10/2001 | Batich et al. .................. 424/423 |
| 6,709,379 B1 * | 3/2004 | Brandau et al. .................... 600/3 |
| 6,808,738 B2 * | 10/2004 | DiTizio et al. ................ 427/2.24 |
| 6,908,506 B2 * | 6/2005 | Zimmermann .................. 106/696 |
| 7,108,970 B2 * | 9/2006 | Levinson ...................... 435/6.11 |
| 7,115,163 B2 * | 10/2006 | Zimmermann .................. 106/35 |
| 7,431,763 B2 * | 10/2008 | Zimmermann .............. 106/690 |
| 7,452,566 B2 * | 11/2008 | Sul ............................... 427/2.26 |
| 7,790,905 B2 * | 9/2010 | Tawa et al. ................. 548/375.1 |
| 7,927,613 B2 * | 4/2011 | Almarsson et al. ............ 424/400 |
| 8,337,936 B2 * | 12/2012 | Bayer et al. ..................... 427/2.1 |
| 8,361,007 B2 * | 1/2013 | Yeung et al. ...................... 604/8 |
| 8,382,823 B2 * | 2/2013 | Kim et al. ..................... 623/1.44 |
| 8,414,958 B2 * | 4/2013 | Schnabelrauch et al. .... 427/2.24 |
| 8,475,824 B2 * | 7/2013 | McKay .......................... 424/423 |
| 8,540,815 B2 * | 9/2013 | Gbureck ........................ 106/690 |
| 8,758,791 B2 * | 6/2014 | McKay .......................... 424/422 |
| 2002/0166480 A1 | 11/2002 | Zimmerman |
| 2004/0173122 A1 * | 9/2004 | Zimmermann .................. 106/696 |
| 2005/0079088 A1 * | 4/2005 | Wirth et al. .................... 420/402 |
| 2006/0141030 A1 * | 6/2006 | Clouatre et al. .............. 424/464 |
| 2007/0185231 A1 * | 8/2007 | Liu et al. ........................ 523/116 |
| 2008/0069852 A1 * | 3/2008 | Shimp et al. ................... 424/423 |
| 2008/0069874 A1 * | 3/2008 | Hall et al. ...................... 424/464 |
| 2008/0195112 A1 * | 8/2008 | Liu et al. ......................... 606/92 |
| 2008/0243242 A1 | 10/2008 | Kappelt et al. |
| 2008/0249638 A1 * | 10/2008 | Asgari ........................ 623/23.75 |
| 2009/0081313 A1 * | 3/2009 | Aghion et al. ................. 424/641 |
| 2009/0105809 A1 * | 4/2009 | Lee et al. ...................... 623/1.17 |
| 2009/0221717 A1 * | 9/2009 | Zimmermann ................ 514/770 |
| 2009/0306725 A1 * | 12/2009 | Hiromoto et al. ............. 606/298 |
| 2010/0021518 A1 * | 1/2010 | Scifert .......................... 424/423 |
| 2010/0049322 A1 * | 2/2010 | McKay ...................... 623/16.11 |
| 2010/0131052 A1 | 5/2010 | Kappelt et al. |
| 2010/0145432 A1 * | 6/2010 | Bayer et al. .................. 623/1.15 |
| 2010/0160922 A1 * | 6/2010 | Liu et al. .......................... 606/92 |
| 2010/0173846 A1 * | 7/2010 | Zimmermann ................. 514/12 |
| 2010/0256774 A1 * | 10/2010 | Wang et al. .................. 623/23.63 |
| 2010/0260922 A1 * | 10/2010 | Owens et al. .................... 427/2.1 |
| 2010/0297082 A1 * | 11/2010 | Guelcher et al. ............. 424/93.1 |
| 2011/0020768 A1 * | 1/2011 | Spagnoli et al. ............. 433/174 |
| 2011/0028568 A1 * | 2/2011 | Gbureck ........................ 514/769 |
| 2011/0104052 A1 * | 5/2011 | Barnett et al. ................ 424/1.21 |
| 2011/0151026 A1 * | 6/2011 | Hansson et al. .............. 424/722 |
| 2011/0182961 A1 * | 7/2011 | McKay .......................... 424/423 |
| 2011/0182962 A1 * | 7/2011 | McKay .......................... 424/423 |
| 2011/0182965 A1 * | 7/2011 | McKay .......................... 424/426 |
| 2011/0244254 A1 * | 10/2011 | Song et al. .................... 428/457 |
| 2011/0244256 A1 * | 10/2011 | Song et al. .................... 428/458 |
| 2011/0270168 A1 * | 11/2011 | Halahmi et al. ........... 604/93.01 |
| 2011/0313538 A1 * | 12/2011 | Oh et al. ...................... 623/23.61 |
| 2012/0107592 A1 * | 5/2012 | Vasilev et al. ................. 428/220 |
| 2012/0191214 A1 * | 7/2012 | Nies ............................ 623/23.62 |
| 2012/0197384 A1 * | 8/2012 | Lee et al. ...................... 623/1.15 |
| 2013/0150978 A1 * | 6/2013 | Nies et al. ...................... 623/23.6 |
| 2013/0261735 A1 * | 10/2013 | Pacetti et al. ................. 623/1.36 |
| 2013/0304134 A1 * | 11/2013 | Tamai et al. .................. 606/301 |
| 2014/0163664 A1 * | 6/2014 | Goldsmith ................... 623/1.11 |

FOREIGN PATENT DOCUMENTS

| | | |
|---|---|---|
| DE | 10 2008 010 210 A1 | 8/2009 |
| DE | 10 2008 043 970 A1 | 5/2010 |
| WO | 02/02478 A1 | 2/2002 |

* cited by examiner

BONE IMPLANT COMPRISING A MAGNESIUM-CONTAINING METALLIC MATERIAL WITH REDUCED CORROSION RATE, AND METHODS AND KIT FOR PRODUCING THE BONE IMPLANT

BACKGROUND OF THE INVENTION

The invention concerns a bone implant which contains a magnesium-containing metallic material with reduced corrosion rate and mineral bone cement, as well as methods and a kit for its production.

Often, only a temporary residence of implant material is necessary in the body when using medical implants. In connection with such implantations, for many years research has been done on the development of bioresorbable implant materials in order to eliminate in the future a complex operation for removing implant materials which cannot be decomposed by the body. Bioresorbable materials have the property of being decomposed gradually after implantation in the body. The resulting decomposition products are resorbed by the body to a large extent.

The decomposition of implant materials can occur actively or passively. In case of active decomposition by the organism, the implant material is degraded by enzymatic or cellular mechanisms. This happens, for example, with implant materials of collagen or mineral bone cements on the base of calcium phosphates. The active decomposition of implant materials is desired particularly when the decomposition occurs within the scope of the natural metabolism and is not based on an inflammation reaction.

A passive decomposition occurs with implant materials which are not stable in the biological environment. This passive decomposition is called herein biodegradation. It is typical for the resorbable polymers of which resorbable suture materials are produced, for example. The decomposition of metals which are not stable in the biological environment occurs also passively. This is referred to herein also as corrosion. Corrosion is to be understood in this context as the conversion of metallic materials into their oxides or salts, i.e., into mineral materials. The term biocorrodibility, i.e., corrosion in the biological environment, has been established for the metallic implant materials. The term is in general used for the desired corrosion of a metallic implant in the body. In particular magnesium and its alloys as well as iron and its ignoble alloys are especially considered to be biocorrodible implant metals. Primarily, the magnesium-containing metallic materials increasingly attract great interest because they clearly exhibit higher strength than resorbable polymers and because magnesium is the only technically available metal which is present in the body in larger quantities and which is incorporated in the form of its ion into numerous biochemical reactions. In contrast to the decomposition products of iron, magnesium ions of the corrosion products of magnesium-containing implants can be eliminated from the body easily.

Biocorrodible implants on the basis of resorbable polymers have been available on the market for some time and have gained commercial relevance in some indications with low mechanical load. However, their widespread use is limited by the low biocompatibility of the decomposition products and the mechanical properties of little reproducibility during the course of the decomposition process.

Because especially orthopedic implants must fulfill high mechanical demands, work has been done intensively for several years on implant materials on the basis of biocorrodible metal alloys. In principle, magnesium alloys are very well suited for this use because their decomposition produces preferably decomposition products in the form of magnesium salts which are biocompatible as natural components of the metabolism. In various studies implants of magnesium alloys have been already examined for cardiovascular uses and as bone implants. In this context, good compatibility has been determined in most cases.

However, when magnesium corrodes, a strong gas generation, preferably hydrogen, is noticeable. This leads in case of large-volume bone implants to the formation of gas bubbles in the tissue, because removal is not sufficiently guaranteed. The corrosion occurs, on the one hand, too fast and, on the other hand, in an uncontrolled way, i.e., not evenly from the outside to the inside, but often concentrated at a few locations. A sufficiently reliable adjustment of mechanical properties of an implant over time is thus not possible. Hence, the development of magnesium implants whose corrosion progresses at a reduced level is being worked on. By means of various modifications, the corrosion of magnesium materials, presently too quick and uncontrollable, should be developed to be controllable.

Up to now, two different approaches are pursued in this context. On the one hand, different magnesium alloys are being tested. On the other hand, magnesium and magnesium alloys are provided with coatings which are designed to inhibit the corrosion of the metal Presently known coatings for inhibiting corrosion of magnesium-based implants are based on the application of polymeric or inorganic layers, the chemical conversion of the metal surface, hot gas oxidation, anodizing, plasma spraying method, varnishes or similar methods DE 101 63 106 A1 discloses magnesium materials in which the corrosion properties are changed by alloying with halides. It is disadvantageous in this context that not only its corrosion properties are changed by alloying but also the mechanical properties of the material.

DE 10 2006 060 501 A1 discloses methods for producing a corrosion-inhibiting layer on magnesium alloys, in this context, a biocorrodible magnesium alloy is coated by means of an anodic plasma-chemical treatment in an aqueous electrolyte. In this context, the electrolyte contains in one embodiment at least $NH_3$, $H_3PO_4$ and $H_3BO_3$. In another embodiment, the electrolyte contains $NaMnO_4$ and $NH_4VO_3$. In the method the magnesium material is switched as an anode. The anodization occurs by plasma discharge in the electrolyte on the surface of the material part to he coated.

DE 10 2008 043 970 A1 discloses methods for producing corrosion-inhibiting coatings on magnesium materials in which the materials are treated in an aqueous or alcoholic conversion solution and are subjected to anodic oxidation in the conversion solution ions are contained in a concentration of $10^{-2}$ mol/l to 2 mol/l. In this context, the ions are selected from at least one of the group $K^+$, $Na^+$, $NH_4^+$, $Ca^{2+}$, $Mg^{2+}$, $Zn^{2+}$, $Ti^{4+}$, $Zr^{4+}$, $Ce^{3+}$, $PO_3^{3-}$, $PO_4^{3-}$, $HPO_4^{2-}$, $H_2PO_4^-$, $OH$, $BO_3^{2-}$, $B_4O_7^{2-}$, $SiO_3^{2-}$, $MnO_4^{2-}$, $MnO_4^-$, $VO_3^-$, $WO_4^{2-}$, $MoO_4^{2-}$, $TiO_3^{2-}$, $Se^{2-}$, $ZrO_3^{2-}$ and $NbO_4^-$.

In spite of the extensive work in connection with the development of new magnesium alloys, up to now solutions have not been found for the cardiovascular use as stents or for the use as bone implants for lowering the corrosion rate to a sufficiently low level in order to be able to guarantee the mechanical function of the implants for the desired period of >6 weeks for cardiovascular use or also even longer periods of >6 months for use as a bone implant.

Hence, there is still the need for alternative approaches for controlling the corrosion of implants based on magnesium.

It is the object of the invention to provide bone implants with magnesium-containing metallic Materials, which exhibit a high corrosion resistance and improved mechanical properties, and methods and means for their production.

SUMMARY OF THE INVENTION

The object is solved according to the invention by a method for producing a hone implant which comprises a magnesium-containing metallic material with a corrosion-inhibiting coating containing magnesium ammonium phosphates and mineral hone cement. According to the method according to the invention, a magnesium-containing metallic material whose surface comprises a magnesium oxide layer and/or a magnesium salt layer is combined with mineral bone cement for producing a solid composite material which contains the mineral bone cement and the magnesium-containing metallic material. In this context, the mineral bone cement contains mineral powder components, which in the presence of water cure to a solid, and water-soluble phosphate ion containing salts, preferably water-soluble phosphate ion containing and ammonium ion containing salts. According to the invention, the magnesium-containing metallic material is contacted with water before and/or during combining with the mineral bone cement in the presence of water-soluble ammonium ion containing and phosphate ion containing salts (preferably ammonium phosphates). Furthermore, the mineral bone cement is brought into contact with water for curing. The water that is necessary for producing the corrosion-inhibiting coating and the water required for triggering the curing reaction of the mineral bone cement are present in the form of pure water or as an aqueous preparation (preferably aqueous solution). In this context, the use of aqueous preparations is preferred over the use of pure water.

The invention also comprises a bone implant which is obtained preferably by a method according to the invention. The bone implant according to the invention comprises a magnesium-containing metallic material and mineral bone cement which contains water-soluble phosphate ion containing salts. In this context, the magnesium-containing metallic material comprises according to the invention a coating that contains magnesium ammonium phosphates (passivation layer).

A kit for producing a bone implant according to the invention is also encompassed by the Invention. The kit according to the invention comprises
a) a bone cement preparation comprising mineral bone cement powder and water-soluble phosphate ion containing salts, and
b) a magnesium-containing metallic material with a magnesium oxide layer and/or a magnesium salt layer and water-soluble ammonium ion containing and phosphate ion containing salts, preferably ammonium phosphates, or
c) a magnesium-containing metallic material with a coating containing magnesium ammonium phosphates and optionally water-soluble ammonium ion containing and phosphate ion containing salts, preferably ammonium phosphates.

The invention is based on the discovery by the inventors that magnesium and magnesium alloys are protected against corrosion by a treatment with ammonium phosphates in aqueous solutions. Upon damage of the magnesium ammonium phosphate layer on the magnesium-containing. metallic material, the layer positioned underneath which contains magnesium oxide and/or magnesium salts (herein also referred to as conversion layer) can be converted to magnesium ammonium phosphate by reaction with the phosphate ions contained in the mineral bone cement so that the corrosion-inhibiting layer is renewed. This also applies when the passivation layer has been removed down to the metallic base because in aqueous environment, in particular also in body fluid, the surface of the magnesium-containing metal spontaneously is covered again with a salt layer (in particular $Mg(OH)_2$ or magnesium hydroxide carbonate), At the same time, the mechanical properties of the obtained bone implant are improved by the combination of the mineral bone cement with the metallic material because the mechanical properties are adjustable by the proper choice of mineral bone cements and adaptable to the corresponding needs of the respective implantation.

For providing the corrosion-inhibiting coating on the surface of the magnesium-containing metallic material, it is necessary to contact the latter during the manufacture of the bone implant with an aqueous ammonium ion containing and phosphate ion containing preparation. By contacting the magnesium-containing metallic material (herein also at times referred to simply as "material") with aqueous solutions which contain ammonium ions and phosphate ions, a layer (herein also referred to as passivation layer) containing magnesium ammonium phosphates, in particular $Mg(NH_4)PO_4 \times 6\ H_2O$, is formed on the surface of the material. The magnesium ammonium phosphates slow down the corrosion of the magnesium-containing metallic material (passivation). The magnesium ammonium phosphate layer on the surface of the metallic magnesium-containing material is only slightly water-permeable. This makes access of water to the metallic magnesium more difficult and slower so that the metallic material corrodes more slowly (corrosion-inhibiting coating). Corrosion of the magnesium-containing metallic material still occurs but at a reduced speed.

The presence of the water-soluble phosphate ion containing salts in the mineral bone cement supports the renewal of the corrosion-inhibiting coating. This is even more improved in the presence of mineral bone cements which contain water-soluble phosphate ion containing as well as ammonium ion containing salts (in particular ammonium phosphates). Hence, mineral bone cements which contain water-soluble phosphate ion containing salts as well as water-soluble ammonium ion containing salts are preferred. The presence of phosphate ion containing and ammonium ion containing salts in the mineral bone cement contributes furthermore advantageously to the increase of the compressive strength of the bone implant In the context of the invention, magnesium-containing metallic materials encompass all metals and metal alloys which contain magnesium in a portion of at least 25% by weight, preferably at least 50% by weight, more preferred at least 75% by weight.

A particularly preferred material is magnesium with a purity of at least 99% by weight (pure magnesium). Further preferred materials are magnesium alloys, in particular alloys of magnesium which comprise the alloying metals aluminum (A), bismuth (B), copper (C), rare earths (E), iron (F), zirconium, (K), lithium (L), manganese (M), silver (Q),silicon (S) yttrium (W) zinc (Z) and calcium, alone or in combination. Multi-element alloys are preferred, i.e., alloys of magnesium with at least two alloying partners; particularly preferred are multi-element alloys which contain yttrium, rare earths, manganese, zinc or zirconium, alone or in combination. A preferred alloy is WE43, i.e., a magnesium alloy which contains yttrium and rare earths. Particularly preferred are magnesium alloys which already exhibit an increased corrosion duration in comparison to pure magnesium, in particular alloys which contain at least magnesium and silicon and optionally additional alloying partners.

The magnesium-containing metallic material can have any geometry for use in the invention. Materials in the form of fibers, threads, filaments, wires are preferred. Of these, fibers are preferred that preferably have a thickness of 10-1,000 μm and a length of 1-100 mm (short fibers). Furthermore, materials are preferred in the form of wires or threads that are made into woven fabrics, braided fabrics, knit fabrics, knitted materials, fleeces, nonwovens, membranes or cords. Further preferred are materials made of web materials obtainable from fibers, threads, filaments or wires, preferably web materials obtainable by pressing and/or sintering of fibers, threads, filaments or wires. Further preferred are materials in the form of an open-cell metal foam. One form of open-cell metal foams are shaped bodies which are constructed from perforated flat metal structures, preferably from perforated sheet metal or expanded metal. In this context, when stacking several layers continuous pore systems are generated. The connection of the individual layers is done, for example, by welding, gluing or mechanical interlocking. Particularly suitable shaped bodies for the invention are rod-shaped shaped bodies which are obtainable by coiling perforated sheet metal or expanded metals and subsequently connecting the individual layers with each other. Further preferred are materials in the form of orthopedic or osteosynthetic implants, in particular plates, screws, nails, pins or cages. Further preferred are materials in particulate form, preferably in the form of chips. Of these, preferred are particles, in particular chips, of a size (maximum expansion) from 10-1,000 μm. Magnesium containing metallic particles have the advantage that they can be mixed homogeneously with the powder component of the mineral bone cement so that a composite material can be obtained with metallic particles uniformly distributed therein.

Biocorrodible magnesium-containing in materials are used in the invention, i.e., materials which are decomposed in the body. In case of use of a magnesium-containing alloy preferably no metals are contained as alloying partner whose decomposition products corrosion products) are biologically incompatible. Preferably, no metals are contained as alloying partners that release biologically incompatible concentrations of the metal during biocorrosion. Alloys of magnesium with silver and/or copper are preferred. Advantageously, the decomposition products that are formed by biocorrosion of these alloys have an antimicrobial effect

The application of the corrosion-inhibiting coating on the magnesium-containing metallic material occurs after the final shaping of the metallic material. The combination of the magnesium-containing metallic material with the mineral bone cement occurs either before or during the implantation, preferably before the implantation.

The formation of the magnesium ammonium phosphates occurs by conversion of magnesium salts and/or magnesium oxides that are located on the surface of the magnesium-containing metallic materials. During storage of magnesium-containing metallic materials, magnesium-containing oxides and/or salt compounds, in particular oxides, hydroxides, carbonates or hydroxide-carbonates, are spontaneously formed on their surface.

These oxides or salt compounds react with ammonium ions and phosphate ions to sparingly soluble magnesium ammonium phosphates, in particular by the following reactions:

(1)

(2)

(3)

(4)

According to the invention, for producing the corrosion-inhibiting coating containing magnesium ammonium phosphates on a magnesium-containing metallic material, ammonium ion containing and phosphate ion containing salts are used. Ammonium ion containing salts and phosphate ion containing salts which are used in the invention are water-soluble. The term water-soluble is to be understood in the context of the invention as solubility in water of at least 0.1 mol/l, preferably of 1.0 mol/l.

Preferred water-soluble ammonium ion containing salts are selected from ammonium acetate, ammonium bicarbonate ammonium carbamate, ammonium carbonate, monobasic, dibasic and tribasic ammonium citrate, ammonium fluoride, ammonium salts of amino acids (in particular ammonium glutamate), ammonium hydroxide, ammonium salts of fatty acids (in particular ammonium oleate), ammonium salts of anionic surfactants (in particular ammonium lauryl sulfate, ammonium cetyl phosphate), ammonium lactate, ammonium sodium phosphate, ammonium potassium phosphate, ammonium nitrate, ammonium sulfate, and ammonium tartrate.

Preferred water-soluble phosphate ion containing salts are selected from sodium Hydrogenphosphate, tri-sodium phosphate, sodium di-hydrogenphosphate, sodium glycerophosphate, sodium pyrophosphates, sodium polyphosphates, potassium hydrogenphosphate, tri-potassium phosphate, potassium dihydrogenphosphate, potassium glycerophosphate, potassium pyrophosphates and potassium polyphosphates.

Preferred combinations of ammonium ion containing and phosphate ion containing salts are ammonium chloride ($NH_4Cl$) and sodium phosphate ($NaH_2PO_4$) or ammonium sulfate ($(NH_4)_2SO_4$ and sodium phosphate ($Na_2HPO_4$).

Water-soluble ammonium phosphates are preferred. In this context, all compounds which contain ammonium ions as well as phosphate ions are to be understood as ammonium phosphates. Preferred ammonium phosphates are selected from: $(NH_4)_3PO_4$, $(NH_4)_2HPO_4$, $(NH_4)H_2PO_4$, ammonium salts of dimeric, oligomeric and polymeric phosphoric acid as well as partially substituted phosphoric acid, in particular ammonium glycerophosphate and their mixtures with each other. Particularly preferred ammonium phosphates are selected from $(NH_4)_3PO_4$, $(NH_4)_2HPO_4$ and $(NH_4)H_2PO_4$ as well as their combinations.

The mineral bone cement which is used according to the invention contains water-soluble phosphate ion containing salts. Preferred phosphate ion containing salts which are contained in the mineral bone cement, are selected from sodium hydrogenphosphate, tri-sodium phosphate, sodium dihydrogenphosphate, sodium glycerophosphate, sodium pyrophosphates, sodium polyphosphates, potassium hydrogenphosphate, tri-potassium phosphate, potassium dihydrogenphosphate, potassium glycerophosphate, potassium pyrophosphates, and potassium polyphosphates.

Ammonium ion containing and phosphate ion containing salts, preferably water-soluble ammonium phosphates, in particular the afore defined ammonium phosphates, are preferably contained in the mineral bone cement. The water-soluble salts (phosphates, preferably ammonium ion containing and phosphate ion containing salts, preferably ammonium phosphates) are contained in the mineral bone cement preferably in a total concentration of from 0.1 to 30% by weight, particularly preferred from 0.1 to 10% by weight, especially preferred from 0.1 to 15% by weight.

Mineral bone cements are understood in the context of the invention as all bone cements which contain mineral components which react with water and/or aqueous solutions with formation of an insoluble solid (herein also referred to as "setting"). Preferred are hydraulic-setting mineral bone cements. As opposed to polymeric bone cements, as for example poly methylmethacrylate bone cements (PMMA cement), no polymerization is necessary for the formation of the solid. The disadvantage of polymeric bone cements is that they are not resorbable. In addition to the mineral components, mineral hone cements can contain polymeric additives which can influence the mechanics, the handling properties, the biological properties, as well as the reaction kinetics. However, in case of mineral hone cements with polymer addition, the main component of the solid is still preferably of the mineral type, i.e. mineral bone cements contain preferably maximally 50% by weight of polymer additives.

Mineral bone cements comprise a powder component which is mixed with an aqueous liquid for triggering the setting reaction. In this context, the powder component contains the solid components that react with water. A water-insoluble solid is generated by the reaction of the reactive solid components of the powder component with water (setting reaction). The set solid is also referred to in the context of the invention as "mineral bone cement". The setting reaction of the mineral bone cement can be triggered before, during or after the combination with the coated magnesium-containing metallic material.

Preferred components of the powder component of the mineral bone cement that in contact with water set to a solid are calcium phosphates and/or magnesium phosphates, in particular α-TCP, β-TCP, tetra-calcium phosphate, amorphous calcium phosphate, mono calcium phosphate, calcium hydrogenphosphate, $Mg_3(PO_4)_2$, and/or $Ca_xMg_{3-x}(PO_4)_2$ (with $0<x<3$). The composition of mineral bone cements is in principle known to a person of skill in the art from the prior art.

The invention employs preferably calcium phosphate cements (herein also referred to as CPC), magnesium phosphate/calcium phosphate cements (herein also referred to as "Mg—CPC") or magnesium phosphate cements (herein also referred to as "MgPC"). The nomenclature of the mineral cements is based on the solids formed in the stetting reaction: calcium phosphate cements form during setting sparingly soluble calcium phosphates; magnesium phosphate cements form during setting sparingly soluble magnesium phosphates.

Mg—CPC and MgPC contain preferably magnesium phosphates and/or magnesium-calcium phosphates, in particular $Mg_3(PO_4)_2$ and/or $Ca_xMg_{3-x}(PO_4)_2$ (with $0<x<3$). They react with ammonium ions and phosphate ions with formation of magnesium ammonium phosphates. The reaction thus occurring in this context is shown in the following equation:

$$Mg_3(PO_4)_2 + (NH_4)_2HPO_4 \rightarrow 2\, Mg(NH_4)PO_4 + MgHPO_4 \quad (5)$$

MgPC on the basis of magnesium oxide (MgO) reacts with ammonium phosphate also to magnesium ammonium phosphate. The MgO contained in the MgPC is preferably fired at high temperature, preferably at temperatures >1,500° C. With ammonium phosphate a reaction occurs according to the following equation:

$$MgO + (NH_4)H_2PO_4 \rightarrow Mg(NH_4)PO_4 + H_2O \quad (6)$$

In this context, in the reaction equations (5) and (6), water as a reaction partner and as crystal water has not been indicated.

Preferred mineral bone cements contain as mineral components magnesium phosphates and/or magnesium calcium phosphates; Mg—CPC or MgPC are particularly preferred.

Calcium phosphate cements (CPC) contain as main components calcium phosphates that are reactive with water, in particular α-TCP, β-TCP, tetra-calcium phosphate, amorphous calcium phosphate, mono-calcium phosphate, calcium hydrogenphosphate and/or their combinations. The setting reaction leads to the formation of sparingly soluble calcium phosphates, in particular hydroxyapatite calcium-deficient hydroxyapatite (CDHA) and/or calcium hydrogenphosphate.

Preferred are CPCs which set to CDHA and are used with an aqueous ammonium phosphate solution as mixture solution. Of these, particularly preferred are CPCs which contain as a reactive component α-TCP.

Further preferred mineral bone cements contain calcium phosphates and/or magnesium phosphates wherein in them at least partially calcium and/or magnesium are substituted therein by bivalent strontium (strontium-containing mineral bone cements).

Mineral bone cements contain preferably other components which are not involved in the setting reaction. Preferably, the mineral bone cement contains pharmaceutical active substances, in particular antibiotics. Alternatively, or in combination, the mineral hone cement contains auxiliary materials, preferably such auxiliary materials that influence the viscosity of the aqueous solution. Preferred auxiliary materials are water-soluble polymers like soluble starch and starch derivatives, cellulose derivates, collagen, gelatin, PEG, PEG-PPG copolymers, water-soluble modified polyacrylates polymethacrylates, PVP and/or PVA. Alternatively, or in combination therewith, the mineral bone cement contains particulate fillers, preferably fillers that are sparingly soluble water, in particular starch, insoluble collagen, insoluble gelatin, mineral particles, in particular silicates, and/or strontium salts.

The powder component of the mineral bone cement exists in the form of a powder or in the form of an anhydrous paste. The embodiment as an anhydrous paste is preferred. Anhydrous in the context of the invention is to be understood as a maximum concentration of water of 1% by weight, preferably of a maximum of 0.1% by weight (relative to the total mass of the paste). In this case the mineral bone cement powder is dispersed in a non-aqueous carrier liquid.

Non-aqueous carrier liquids are anhydrous (containing less than 1% by weight, preferably less than 0.1% by weight of water relative to the mass of the carrier liquid). As carrier liquids water-soluble or water-insoluble liquids are suitable.

Preferred carrier liquids are non-polar or hydrophobic materials, in particular oils. Preferred carrier liquids are selected from aliphatic hydrocarbons, esters, ethers, sparingly water-soluble organic acids, sparingly water-soluble monovalent or multivalent alcohols, and their combinations, wherein the compounds have in each case a molecular weight of less than 2,500 g/mol. Sparingly water-soluble compounds are to be understood in the context of the invention as compounds whose maximum solubility amounts to 0.1 mol/l, preferably 0.1 mol/l in water.

In this context, preferably the paste contains at least one setting accelerator, preferably phosphate salts, organic acids (in particular citric acid, tartaric acid, itaconic acid, ascorbic acid, lactic acid and/or amino acids) or their salts. Preferred setting accelerators are sodium phosphates, potassium phosphates, ammonium phosphates, sodium citrates, potassium citrates, ammonium citrates, sodium tartrates, potassium tartrates and/or ammonium tartrates.

Furthermore, the paste contains preferably at least one surfactant. Preferred are anionic, cationic, amphoteric and/or non-ionic surfactants.

The paste is composed preferably of dispersed solids and carrier liquid in a mass ratio of at least 2:1. A mass ratio of at least 3:1 is preferred. Preferably a maximum of 95% by weight of solids are contained in the paste The term powder component is understood in the context of the invention to mean also the form of the anhydrous paste because the latter contains the bone cement powder that is reactive with water.

Mineral bone cements can be present as a two-component solid/liquid system (solid component with mineral bone cement powder and liquid component containing water) or as a single or two-component paste system. In a two-component paste systems the powder component is formulated, as described above, as an anhydrous paste and the aqueous component is an aqueous solution, pure water or is also formulated as a paste, wherein in the past solids that are not reactive with water, in particular fillers, preferably selected from starch, water-insoluble collagen, water-insoluble gelatin and/or mineral particles, in particular silicates, are dispersed in an aqueous solution, Preferably, the first component of a two-component paste system (powder component) is formulated, as described above, as an anhydrous paste and the second component (aqueous component) is an autologous body fluid, in particular bone marrow, a suspension of autologous cells, blood or serum.

The mineral bone cement which is used in the invention contains water-soluble phosphate ion containing salts, preferably water-soluble ammonium ion containing and phosphate ion containing salts. Then the mineral bone cement mixed with water contains dissolved phosphate ions, preferably dissolved ammonium ions and phosphate ions.

This is achieved in that
a) water-soluble phosphate ion containing salts, preferably water-soluble ammonium ion containing and phosphate ion containing salts, preferably water-soluble ammonium phosphates, are contained as a solid in the powder and/or
b) the aqueous solution with which the solid is mixed contains phosphate ions, preferably ammonium ions and phosphate ions, preferably dissolved ammonium phosphates, and/or
c) phosphate ion containing salts are contained in the powder component of the mineral bone cement and/or in the aqueous solution with which the bone cement is mixed, wherein preferably additionally ammonium ion containing salts are contained in the powder component of the mineral bone cement and/or in the aqueous solution with which the bone cement is mixed.

In case b) where an aqueous phosphate ion containing solution is added to the mineral bone cement for triggering the setting reaction, this solution contains preferably at least 0.1 mol/l, preferably 0.5-5 mol/l, more preferred 2-5 mol/l of phosphate ions. When ammonium ion containing and phosphate ion containing salts, in particular ammonium phosphates, are contained in the aqueous solution, the total concentration of the ammonium ion containing and phosphate ion containing salts (i.e. ammonium phosphates) is at least 0.1 mol/l, preferably 0.5-5 mol/1, more preferred 2-5 mol/l. Thereby it is achieved advantageously that only a portion of the phosphates is converted in the setting reaction and a residual portion remains as a depot in the bone cement matrix.

In the preferred aforementioned cases a) to c) in which ammonium ions are contained in the mineral bone cement, the mixed mineral bone cement contains ammonium ions, preferably ammonium phosphates, in a concentration of preferably at least 0.1 mol/l, preferably 0.5-5 mol/l, particularly preferred 2-5 mol/l.

According to the method according to the invention, first magnesium-containing metallic materials are provided whose surface comprises a magnesium oxide layer and/or a magnesium salt layer. A "magnesium salt layer" is to be understood in the context of the invention as a superficial layer, containing magnesium salts, on the magnesium-containing metallic material. The magnesium salts and/or magnesium oxides which are located on the surface of the material have the property that they react with ammonium ions and phosphate ions at room temperature to magnesium ammonium phosphates. Because this reaction represents a conversion of the magnesium salts or magnesium oxides during setting into sparingly soluble magnesium ammonium phosphates, the magnesium oxide layer and/or magnesium salt layer is also referred to as conversion layer. The magnesium salts are preferably hydroxides, carbonates or hydroxide-carbonates of magnesium or their combinations with each other. It is particularly preferred that the magnesium-containing metallic material comprises MgO, $Mg(OH)_2$, $MgCO_3$, magnesium hydroxide-carbonate, $Mg_3(PO_4)_2$, $MgHPO_4$, $MgCl_2$, $MgSO_4$, magnesium citrate, or their combinations, on the surface.

The magnesium oxide layer and/or magnesium salt layer is formed preferably spontaneously on the magnesium-containing metallic material during storage of the material. Alternatively, or in combination therewith, a layer that contains magnesium salts and/or magnesium oxide is applied by a coating method onto the surface of the material. Coating of the metallic material with magnesium oxides and/or magnesium salts is suitable particularly to achieve a high layer thickness of the conversion layer and to further improve thereby the corrosion resistance. The coating with the magnesium oxides and/or magnesium salts is carried out in this context preferably electrochemically or is assisted preferably by an electric potential.

Preferably, the conversion layer is generated by the treatment of the metallic magnesium-containing material with an organic or mineral acid or the solution of an organic or mineral acid in water or an organic solvent like alcohol or acetone. As an alternative to the treatment with an acid, the treatment occurs preferably with a salt or a salt solution, wherein the magnesium salt of the respective anion has a lower solubility than the salt of another cation used for the treatment.

Particularly preferred is the treatment of the metallic magnesium-containing material with acids whose magnesium salts are sparingly soluble in the appropriately selected treatment liquid. Preferably, the treatment of the magnesium-containing metallic material occurs in an aqueous or alcoholic citric acid solution or in an aqueous or alcoholic solution of a salt of citric acid that is easily soluble in water, preferably sodium citrate. The treatment with citric acid or citrates causes the formation of a layer of magnesium citrate on the surface of the material. Upon a subsequent contacting with ammonium ions and phosphate ions, the magnesium citrate is converted to magnesium ammonium phosphate. Further preferred is the treatment of the metallic magnesium-containing material directly with oleic acid or with oleates, preferably sodium oleate in aqueous or alcoholic solution. In this case, the conversion layer contains magnesium oleate.

Preferably, a coating with magnesium salts and/or magnesium oxides is applied to the material in that the magnesium salts and/or magnesium oxides are applied in combination with auxiliary materials, preferably binding agents, onto the material. During coating, a layer is then formed on the magnesium-containing metallic material which contains magnesium salts and/or magnesium oxides and auxiliary materials, preferably binding agents.

The magnesium-containing metallic material with the conversion layer is combined with phosphate ion containing mineral bone cement, wherein the production of the composite material occurs in the presence of a water-containing preparation, preferably of an aqueous solution, which contains ammonium ion containing and phosphate ion containing salts, preferably ammonium phosphates.

By contacting the magnesium salts and/or magnesium oxides on the surface of the material with ammonium ions and phosphate ions in aqueous environment, they are converted into the magnesium ammonium phosphates which form a corrosion-inhibiting coating on the surface of the material. The corrosion-inhibiting coating which contains magnesium ammonium phosphates is also referred to as passivation layer. The formed magnesium ammonium phosphates are sparingly water-soluble salts, containing, magnesium ions, ammonium ions and phosphate ions. The materials that are produced by a method according to the invention and coated with magnesium ammonium phosphates comprise on their surface a layer, preferably containing magnesium ammonium phosphates of the molecular formula $Mg(NH_4)PO_4 \times 6\ H_2O$.

The water-containing preparation that is used for producing the corrosion-inhibiting coating contains water-soluble ammonium ions and phosphate ions in a concentration in each case from between 0.1 and 5.0 mol/l. Particularly preferred, the concentration range is from 0.5 to 5.0 mol/l, preferred particularly is the range of 2.0 to 5.0 mol/l.

Contacting the magnesium-containing metallic in with the ammonium ion containing and phosphate ion containing, water-containing preparation occurs, in case that the preparation is an aqueous solution, preferably by introducing, preferably immersing, the metallic material into the aqueous solution. The contact time amounts preferably to at least 1 min., preferably at least 10 min., particularly preferred at least 60 min., especially preferred between 120 min, and 24 hrs. Preferably contacting takes place with constant stirring of the aqueous solution.

When water-soluble (ammonium ion containing and phosphate ion containing salts are applied as a solid in the form of a coating onto the metallic material, they exhibit preferably a water solubility of >10 g/l. The ammonium ion containing and phosphate ion containing salts are dissolved by addition of an aqueous solvent, preferably water or mineral bone cement powder mixed with water, so that an aqueous preparation is formed which contains ammonium ions and phosphate ions and is in contact with the metallic material.

When a layer which contains ammonium ion containing and phosphate ion containing salts is applied onto the surface of the magnesium-containing metallic material prior to producing the composite material, it is advantageous to embed the ammonium ion containing and phosphate ion containing salts in the conversion layer. In order to achieve this, magnesium salts and/or magnesium oxides are mixed with ammonium ion containing and phosphate ion containing salts, preferably ammonium phosphates, and applied as a layer onto the magnesium-containing metallic material. This is done either in dry form, i.e., by direct application of the solids preferably in powder form or with the aid of a non-aqueous carrier liquid. Preferred non-aqueous carrier liquids used for this purpose are varnishes. As varnishes, film-forming materials that are span ugly soluble in water are suitable which themselves are biocompatible and likewise their decomposition products. Preferred varnishes are biodegradable polymers, in particular polymers that contain polylactides, polyglycolides, polycaprolactones, polyhydroxybutyric acid, or copolymers thereof. Further preferred biodegradable polymers are polyanhydrides. Further preferred varnishes are fats and waxes.

Particularly preferred is the combination of magnesium oxides and ammonium phosphates in the form of solids in powder form which are dispersed finely in varnishes. A varnish layer is generated on the material by the application of a varnish with dispersed magnesium salts and/or magnesium oxides and ammonium ion containing and phosphate ion containing salts. With admission of water, the ammonium ion containing and phosphate ion containing salts, preferably ammonium phosphates, are dissolved and react with the magnesium salts and/or magnesium oxides under formation of magnesium ammonium phosphates. When the layer of magnesium ammonium phosphates that is produced in this way is damaged or degrades, a new layer is formed with new admission of water.

As an alternative thereto, a layer containing ammonium ion containing and phosphate ion containing salts will be applied on the surface of the conversion layer of the magnesium-containing metallic material prior to producing the composite material in that ammonium ion containing and phosphate ion containing salts, preferably ammonium phosphates, are applied by using a binding agent and subsequent drying. Afterwards, a heat treatment is carried out at temperatures which are above the melting point of the applied salts. Preferably, the heat treatment occurs at a temperature of >150° C., preferably >190° C. In this context, the applied salts melt and form a continuous layer in the form of a glass-like coating. Preferred binding agents are phosphates (in particular polyphosphates), water-soluble silicates (in particular waterglass) and/or siliceous brine.

As an alternative thereto, a layer containing ammonium ion containing and phosphate ion containing salts is applied to the surface of the conversion layer of the magnesium-containing metallic material prior to producing the composite material in that ammonium ion containing and phosphate ion containing salts in combination with film-forming polymers are employed. Preferred polymers are resorbable polymers. As a result of the coating of the material by means of the film-forming polymers, ammonium ion containing and phosphate ion containing salts are retained for a long time on the surface of the coating.

Preferably, a magnesium ammonium phosphate layer with a layer thickness of at least 0.01 μm is applied to the material by the method according to the invention. Particularly preferred is a layer thickness of 0.01 to 10 μm.

When the ammonium phosphates, or the ammonium ion containing and phosphate ion containing salts, are applied in a non-aqueous carrier liquid together with magnesium salts and/or magnesium oxides, in particular in a varnish, the thickness of the layer amounts preferably to 20 μm to 2.0 mm. This layer contains the magnesium salts and/or magnesium oxides as well as the ammonium ion containing and phosphate ion containing salts, preferably ammonium phosphates.

For producing the corrosion-inhibiting coating in the production of the hone implant, the following variants, which are successful alone as well as in any combination with each other, are preferred:

1. The magnesium-containing metallic material whose surface comprises a magnesium oxide layer and/or a magnesium salt layer is contacted prior to producing the composite material with an aqueous solution which contains ammonium ion containing and phosphate ion containing salts, preferably ammonium phosphates. In this manner, a corrosion-inhibiting coating on the metallic material is already produced before its combination with the mineral bone cement.
2. On the surface of the magnesium-containing metallic material whose surface comprises a magnesium oxide layer and/or a magnesium salt layer, a coating which contains ammonium ion containing and phosphate ion containing salts, preferably ammonium phosphates, is applied first. The magnesium-containing metallic material coated with ammonium ion containing and phosphate ion containing salts is then contacted before or during the production of the composite material with an aqueous solution. The ammonium ions and phosphate ions which are located on the surface of the metallic material are dissolved by the presence of the water so that in situ an ammonium ion containing and phosphate ion containing aqueous solution is formed which leads to the formation of the magnesium ammonium phosphates on the surface of the magnesium-containing metallic material. In this context, the aqueous solvent is preferably an aqueous solution which is contacted with the metallic material prior to combining with the mineral bone cement, or the aqueous solution with which the powder component of the mineral bone cement is contacted (preferably mixed). When coating the magnesium-containing metallic material with a layer of ammonium ion containing and phosphate ion containing salts, it is thus possible to generate the corrosion-inhibiting coating prior to or during the production of the composite material.

3. The magnesium-containing metallic material whose surface comprises a magnesium oxide layer and/or a magnesium salt layer is combined with a mineral bone cement which contains ammonium ion containing and phosphate ion containing salts, preferably ammonium phosphates. In this context, the mineral bone cement (in this context the powder component of the mineral bone cement is meant) is mixed with an aqueous solution before or after combining with the magnesium-containing metallic material for producing the composite material. In this manner, the corrosion-inhibiting coating on the magnesium-containing metallic material is generated during the production of the composite material. By the reaction of the water with the powder component of the mineral bone cement, the latter cures so that a solid composite material is formed.

When the magnesium-containing metallic material is contacted with a mineral bone cement which is embodied as an anhydrous paste, the magnesium-containing metallic material is preferably coated with a corrosion-inhibiting coating with magnesium ammonium phosphates and dried prior to being combined with the mineral bone cement, and/or mixed with the mineral bone cement which contains ammonium ion containing as well as phosphate ion containing water-soluble salts (in this manner, the corrosion-inhibiting coating will form on the metallic material upon admission of water).

Preferably, the magnesium-containing metallic material whose surface comprises a magnesium in oxide layer and/or a magnesium salt layer prior to producing the composite material is contacted with an aqueous solution which contains ammonium ion containing and phosphate ion containing salts so that on the metallic material a corrosion-inhibiting coating is first generated which contains magnesium ammonium phosphates. Afterwards, the so coated magnesium-containing metallic material is combined with a mineral bone cement which contains phosphate ion containing as well as ammonium ion containing salts. An especially high corrosion resistance of the magnesium-containing metallic material is thereby advantageously generated in the bone implant because even in case of defects on the corrosion-inhibiting layer an especially effective repair of the layer can occur by means of the ammonium ions and phosphate ions contained in the hone cement. Furthermore, the mechanical properties of the bone implant are considerably improved.

In the method according to the invention, the presence of water is thus necessary for two reactions: for producing the corrosion-inhibiting magnesium ammonium phosphate coating on the magnesium-containing metallic material and for the setting reaction of the mineral bone cement. Both reactions can take place also at the same time in the method according to the invention. The production of the corrosion-inhibiting coating on the material can occur before and/or during combining with the mineral bone cement. In any case, the magnesium-containing metallic material and the mineral bone cement are so combined that the setting reaction of the mineral bone cement is not yet completed prior to combining.

The setting reaction of the mineral bone cement is started preferably by addition of water or an aqueous solution before the implantation. This can also happen during the industrial manufacturing process of the bone implant. In case that the magnesium-containing metallic material is contacted with a mineral bone cement which is embodied as an anhydrous paste, it is possible to implant the metallic material combined with the bone cement paste without prior contact with water or an aqueous solution. In this case, the setting reaction of the mineral bone cement is spontaneously started in the body by the water contained in body fluids.

With completion of the setting reaction, the solid composite material is obtained which contains the mineral bone cement and the magnesium-containing metallic material in the context of the invention, a composite material is to be understood as a solid body which contains the magnesium-containing metal coated with magnesium ammonium phosphates as well as the mineral hone cement.

For producing the composite material, the magnesium-containing metallic material is combined with the bone cement preferably by mixing and subsequent addition of an aqueous liquid in case that two solid components are present (in particular metal chips and the powder component of the mineral bone cement). In case that the mineral bone cement already has been mixed and the setting reaction has started or the powder component of the mineral bone cement is embodied as an anhydrous paste, combining of the material with the bone cement occurs by contacting the bone cement paste with the metallic material so that the mineral bone cement encloses the magnesium-containing metallic material at least partially. The metallic material and the mineral bone cement are combined preferably such that the material is completely enclosed by the bone cement. In the composite material, the magnesium-containing metallic material and the mineral bone cement are therefore present in such a way that at least a part of the metallic material is enclosed by (cured) mineral bone cement.

The bone implant according to the invention is a solid composite material which contains, besides the magnesium-containing metallic material with the corrosion-inhibiting coating, mineral bone cement which contains water-soluble phosphate ion containing salts. Preferably, the mineral bone cement contains ammonium ion containing and phosphate ion containing salts, particularly preferred ammonium phosphates.

The preferred concentrations of water-soluble phosphate ion containing salts, preferably water-soluble ammonium ion containing and phosphate ion containing salts, which are contained as additives in the mineral bone cement of a bone implant according to the invention amount to a total of 0.025% by weight to 25% by weight, preferably 0.025% by weight to 5% by weight, relative to the bone cement mass. This is accomplished in the production of the bone implant according to the invention preferably in that the powder component of the mineral bone cement is mixed with an aqueous solution that contains ammonium ion containing and phosphate ion containing salts, preferably ammonium phosphates, whose total concentration amounts preferably to 0.1-10% by weight for CPC or whose concentration amounts preferably to 0.5 to 5.0 mol/l, further preferred 5 to 60% by weight, for MgPC or Mg—CPC. The mixing ratio of liquid and powder for mixing a mineral bone cement amounts preferably to between 0.3 ml/g and 0.5 ml/g.

The thickness of the layer containing magnesium ammonium phosphates (passivation layer) on the material amounts preferably to 2 mm and less. Preferably, the thickness of the passivation layer amounts to more than 0.01 µm, particularly preferred more than 0.1 µm, especially preferred to at least 1 µm. It is further preferred that the thickness of the passivation layer amounts to less than to 50 µm, preferably less than 20 µm. Further preferred, the thickness of the passivation layer amounts to between 0.01 to 25 µm, further preferred between 1 and 10 µm.

The passivation layer is located on the surface of the magnesium-containing metallic material. Between the superficial layer containing magnesium ammonium phosphate and the metal, there is preferably a layer (conversion layer) containing magnesium salts and/or magnesium oxides. The conversion layer has preferably a thickness of 0.1 to 100 µm, preferably 0.1 to 50 µm. In this context, the magnesium salts and/or magnesium oxides are preferably selected from MgO, $Mg(OH)_2$, $MgCO_3$, magnesium hydroxide-carbonate, $Mg_3(PO_4)_2$, $MgHPO_4$, $MgCl_2$, $MgSO_4$, magnesium citrate, and their combinations. The conversion layer contains preferably in addition to magnesium salts and/or magnesium oxides furthermore ammonium ion containing and phosphate ion containing salts, preferably ammonium phosphates.

Preferred bone implants contain one of the composite materials configured as follows:

1. Composite material containing mineral bone cement with phosphate ion containing salts, preferably ammonium ion containing and phosphate ion containing salts (preferably ammonium phosphates), and magnesium fibers. When being applied, bone implants of this kind are cut to size, preferably before implantation, to a shape conforming to the bone defect site.
2. Composite material containing mineral bone cement with phosphate ion containing salts, preferably ammonium ion containing and phosphate ion containing salts (preferably ammonium phosphates), and a web material of a magnesium-containing metallic material. Preferred web materials are woven fabrics, braided fabrics, knit fabrics, knitted materials, fleeces, nonwovens, membranes, cords that contain wires of magnesium-containing metallic material or web materials that are obtainable by pressing and/or sintering. The web material contains an open-pore scaffolding of the magnesium-containing metallic material and comprises an interconnected pore system. For producing the composite material, the web material is impregnated with mineral bone cement wherein either a mineral bone cement mixed with an aqueous solution (direct production of the solid composite material) or mineral bone cement in the form of an anhydrous paste (bone cement powder dispersed in an anhydrous, preferably hydrophobic, carrier liquid as described above) is used. In the second alternative, the solid composite material is obtained by contacting with an aqueous solution.
3. Composite material containing mineral hone cement with phosphate ion containing salts, preferably ammonium ion containing and phosphate ion containing salts (preferably ammonium phosphates), and a magnesium-containing metallic material in the form of a plate, a nail, a screw or a cage.
4. Composite material containing mineral bone cement with phosphate ion containing salts, preferably ammonium ion containing and phosphate ion containing salts (preferably ammonium phosphates), and the magnesium-containing metallic material in particulate form (preferably in the form of chips or short fibers). The composite material is produced preferably in that the powder component of the mineral bone cement is mixed with the chips or short fibers and afterwards is mixed with an aqueous solution for triggering the setting reaction. As an alternative thereto, the composite material is preferably produced in that a mineral bone cement is mixed in the form of an anhydrous paste (bone cement powder dispersed in an anhydrous, preferably hydrophobic, carrier liquid as described above) with the chips or short fibers and afterwards is mixed with an aqueous solution for triggering the setting reaction.

The kit according to the invention contains the necessary means for producing a hone implant according to the invention, wherein water or a water-containing preparation are contained optionally. At least contained are: a mineral bone cement preparation, water-soluble phosphate ion containing salts, and a magnesium-containing metallic material. When the magnesium-containing metallic material is contained in the kit without a corrosion-inhibiting coating containing magnesium ammonium phosphate, water-soluble ammonium ion containing and phosphate ion containing salts are also a component of the kit. When the magnesium-containing metallic material contained in the kit is already provided with a coating containing magnesium ammonium phosphates, ammonium ion containing and phosphate ion containing salts are contained optionally in the kit.

The term kit encompasses in the context of the invention a single-component or multi-component preparation (implant material) containing the afore mentioned components as well as the packaged components. Preferred packagings like bags, syringes or the like are known to a person of skill in the art. When using the kit according to the invention, the bone cement preparation contained in it and the magnesium-containing metallic material are combined with a method according to the invention to a bone implant according to the invention.

In case that a magnesium-containing metallic material with a corrosion-inhibiting coating containing magnesium ammonium phosphates is contained, a further addition of ammonium ion containing and phosphate ion containing salts is not necessary, but preferred.

The afore mentioned preferred embodiments concerning the magnesium-containing metallic material, the ammonium ion containing and phosphate ion containing salts, and the mineral bone cement apply likewise also to the kit according to the invention.

The kit according to the invention is configured preferably as a single-component system (single-component implant material) that contains the means necessary for the bone implant manufacture; the bone cement preparation, the magnesium-containing metallic material and the ammonium ion containing and phosphate ion containing salts in one single component. This component is contacted with an aqueous solution for producing the solid composite material. Preferably, the single-component kit is in the form of a solid powder preparation or in the form of an anhydrous paste (wherein the anhydrous paste has a composition as described above).

It is preferred that in a kit according to the invention ammonium ion containing and phosphate ion containing salts, preferably ammonium phosphates, are contained as solids in the bone cement preparation or they are existing in the form of an aqueous solution as a separate component of the kit. It is further preferred that ammonium ion containing and phosphate ion containing salts, preferably ammonium phosphates, are present as a coating on the magnesium-containing metallic material.

The bone cement preparation of a kit according to the invention is a powder component of a mineral bone cement formulated as an anhydrous paste (preferably as defined above). In this context, the mineral bone cement powder is dispersed in a non-aqueous, preferably hydrophobic, carrier liquid. In this case it is particularly preferred that at least the bone cement preparation is introduced into a watertight packaging.

Further preferred is that the mineral bone cement and the magnesium-containing metallic material are present as one component of the kit which is contacted for producing the composite material with an aqueous solution.

Particularly preferred kits according to the invention contain a bone cement preparation formulated as an anhydrous paste and a magnesium-containing metallic material that is particulate and/or porous. When a particulate metallic material is used, the latter is preferably dispersed in the bone cement preparation. When a porous metallic material (in particular an open-pore web material as defined above) is used, the bone cement preparation is introduced preferably into the pores of the metallic material. In this manner, a formable composite material is produced which only after contact with an aqueous liquid in particular after the implantation in the body) is caused to cure.

The invention also comprises the use of a kit according to the invention for producing a bone implant.

With the invention it is possible to provide resorbable bone implants containing metallic magnesium which exhibit a reduced and controllable corrosion speed. At the same time, a high mechanical stability is guaranteed by the mineral bone cement (in particular high compressive strength) so that the materials are particularly well suited for implantation in the bone.

BRIEF DESCRIPTION OF THE DRAWINGS

With the aid of the following figures and embodiments, the invention will be explained in more detail without limiting the invention thereto.

DESCRIPTION OF PREFERRED EMBODIMENTS

Embodiment 1: Coating of Magnesium Wire with Magnesium Ammonium Phosphates

Magnesium wire (Mg wire) with a purity of 99.9% and a diameter of 1.6 mm (company: Drahtwerk ELISENTAL W. Erdmann GmbH & Co., Neuenrade) was stored at room temperature and afterwards incubated in 2.0 mol/l di-ammonium hydrogenphosphate solution for 2 hrs. with constant stirring. The thus treated Mg wire was incubated in simulated body fluid (SBF) at 37° C. for 24 hrs. An untreated magnesium wire served as a comparative example.

Figure 1:
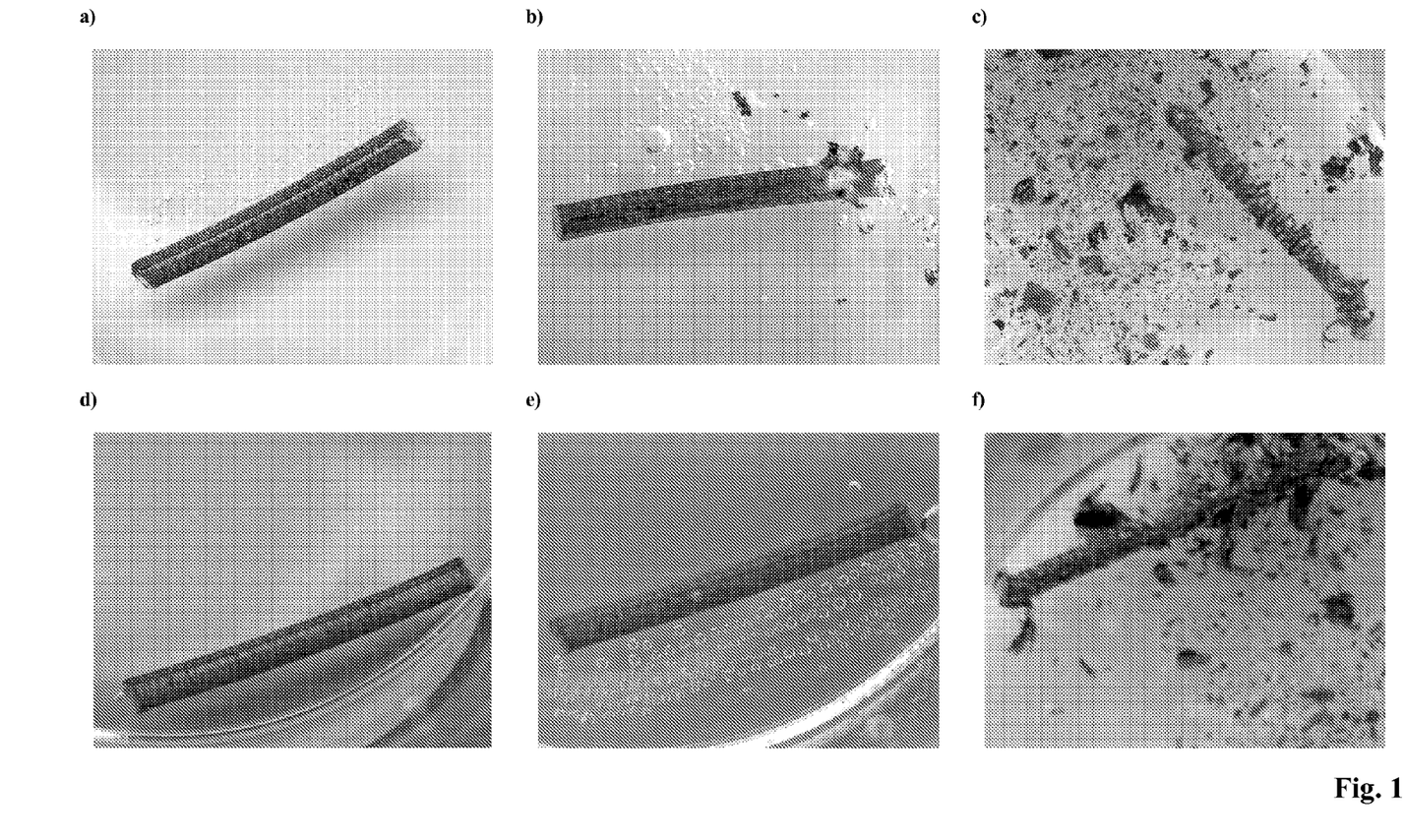
FIG. 1 Corrosion of an untreated magnesium wire in simulated body fluid (comparative example, a) 0 hours, b) 1 hour, c) 24 hours) and of a magnesium wire treated with ammonium phosphates (d) 0 hours, e) 1 hour, f) 24 hours).

The corrosion of the magnesium wire coated according to a method according to the invention in comparison to the untreated wire is shown in FIG. 1. While the untreated Mg wire corrodes immediately (blistering), a delay of the corrosion can be determined for the magnesium wire treated according to the invention. However, even for the treated Mg wire, a distinct corrosion is still determined after 24 hrs. This shows that, in the absence of mineral bone cement, the coating with magnesium ammonium phosphates alone cannot yet provide a sufficient corrosion resistance.

Embodiment 2: Implant material, containing a magnesium wire coated with magnesium ammonium phosphates and magnesium calcium phosphate cement with ammonium phosphates Magnesium wire (Mg wire) with a purity of 99.9% and a diameter of 1.6 mm (company: Drahtwerk ELISENTAL W. Erdmann GmbH & Co., Neuenrade) was stored at room temperature and afterwards incubated in 2.0 mol/l di-ammonium hydrogenphosphate solution for 2 hrs, with constant stirring.

Magnesium calcium phosphate cement powder was mixed with 3.5 mol/l ammonium phosphate solution (2.0 mol/l $(NH_4)_2HPO_4$+1.5 mol/l $(NH_4)H_2PO_4$) in a ratio liquid/powder=0.4 ml/g and was combined with untreated Mg wire or with ammonium phosphate treated Mg wire (comparative example). At one end of the produced cylindrical shaped body (Ø=10 mm, H=20 mm), a piece of a length of approx. 2 mm of the untreated or treated Mg wire protruded.

The produced wire cement composites were incubated in simulated body fluid (SBF) at 37° C. The SBF was buffered with TRIS and was exchanged 2× per week.

Figure 2:
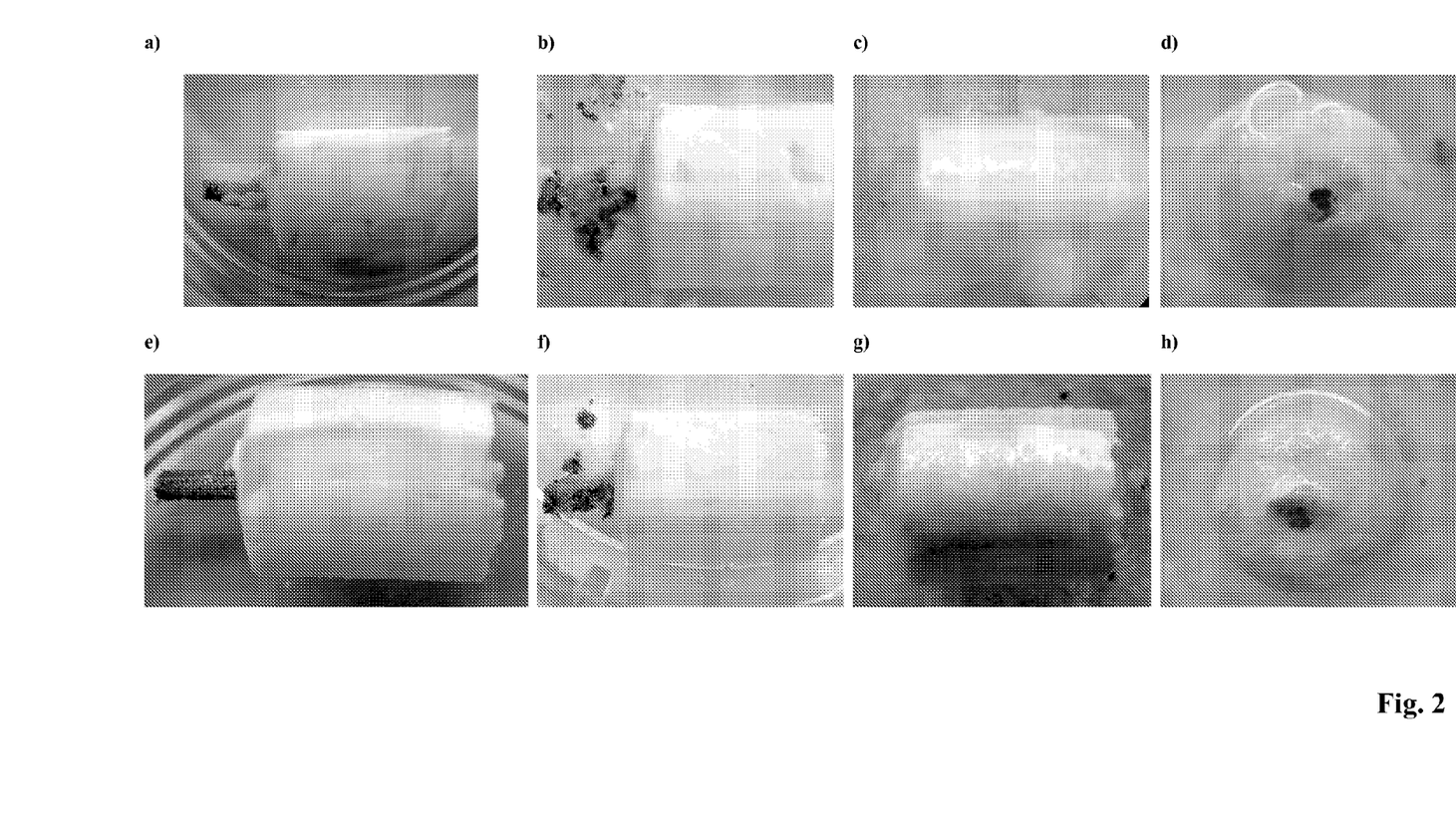
FIG. 2 Corrosion of an untreated magnesium wire in combination with magnesium calcium phosphate cement with ammonium phosphate (comparative example, a) 0 hours, b) 24 hours, c) and d) (plan view) 6 weeks) and of a magnesium wire treated with ammonium phosphates in combination with magnesium calcium phosphate cement with ammonium phosphate (e) 0 hours, f) 24 hours, g) and h) (plan view) 6 weeks in simulated body fluid.

The corrosion behavior of both materials is shown in FIG. 2.

Even after 6 weeks, the composite of the untreated Mg wire and magnesium calcium phosphate cement as well as the composite of treated Mg wire and magnesium calcium phosphate cement were preserved as such. The free wire end of the untreated magnesium wire corroded faster than the free wire end of the coated magnesium wire.

Surprisingly, it was found that even though the exposed end of the magnesium wire had corroded, the corrosion of the magnesium however did not continue essentially within the mineral bone cement. The corrosion of the magnesium wire is inhibited by the passivation layer of magnesium ammonium phosphates which is located at the boundary of the magnesium to the bone cement.

During incubation white salt crystals of magnesium ammonium phosphate deposited on the cement body as well as on the broken-off Mg wire pieces. This shows clearly that the mineral bone cement which contains ammonium phosphates contributes to reducing the corrosion speed.

Embodiment 3: Implant material, containing a magnesium wire coated with magnesium ammonium phosphates and calcium phosphate cement with sodium phosphate Magnesium wire (Mg wire) with a purity of 999% and a diameter of 6 mm (company: Drahtwerk ELISENTAL W. Erdmann GmbH & Co., Neuenrade) was stored at room temperature and afterwards incubated in 2.0 mol/l di-ammonium hydrogenphosphate solution for 2 hrs. with constant stirring.

Calcium phosphate cement powder was mixed with 4% (w/v) di-sodium hydrogenphosphate solution in a ratio liquid/powder=0.4 ml/g and used to envelope untreated Mg wire as well as Mg wire treated with ammonium phosphate. At one end of the produced cylindrical shaped body (Ø=10 mm, H=20 mm) a piece of a length of approx. 2 mm of the untreated or treated Mg wire protruded.

The produced wire cement composites were incubated in simulated body fluid (SBF) at 37° C. The SBF was buffered with TRIS and was exchanged 2× per week.

Figure 3:
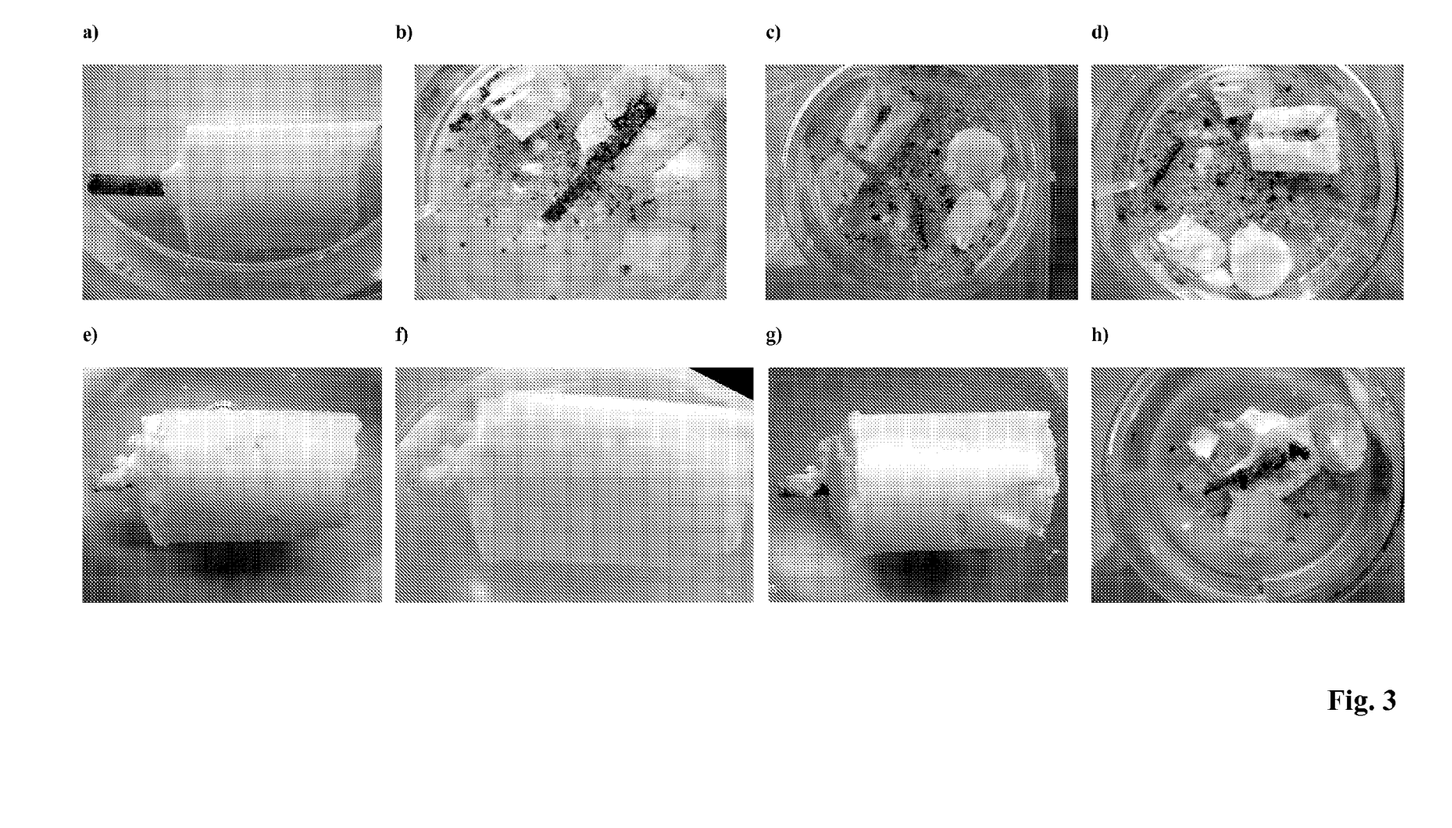
FIG. 3 Corrosion of an untreated magnesium wire in combination with calcium phosphate cement with sodium phosphate (comparative example, a) 0 hours, h) 26 hours, c) 14 days, d) 17 days) and of a magnesium wire treated with ammonium phosphates in combination with calcium phosphate cement with sodium phosphate (e) 0 hours, f) 26 hours, g) 14 days, h) 17 days) in simulated body fluid.

The corrosion behavior of both materials is shown in FIG. 3.

Already after 26 hrs., the composite of untreated Mg wire and calcium phosphate cement mixed with sodium hydrogenphosphate solution was blown apart by the corrosion products formed during the corrosion of the Mg wire. No satisfactory corrosion resistance of the magnesium wire to enable suitability for bone implants can thus be achieved in the absence of ammonium ions After 17 days the composite of treated Mg wire and calcium phosphate cement mixed with di-sodium hydrogenphosphate solution was blown apart by the corrosion products formed during the corrosion of the Mg wire. The corrosion resistance was therefore increased significantly by the prior treatment of the magnesium wire in aqueous solution with ammonium phosphates so that the composite thereby remains stable for several weeks.

The illustrated results show therefore that only by the presence of ammonium ion containing and phosphate ion containing salts during the production of the composite material a significant corrosion protection is achieved which enables a service life of the magnesium-containing implant of several weeks.

Embodiment 4: Implant material, containing a magnesium wire coated with magnesium ammonium phosphates and calcium phosphate cement with ammonium phosphates Magnesium wire (Mg wire) with a purity of 99.9% and a diameter of 16 mm (company: Drahtwerk ELISENTAL W. Erdmann GmbH & Co., Neuenrade) was stored at room temperature and afterwards incubated in 2.0 mol/l di-ammonium hydrogen phosphate solution for 2 hrs with constant stirring.

Calcium phosphate cement powders were mixed with 3,5 mol/l di-ammonium hydrogen phosphate solution in a ratio of liquid/solid 0.4 ml/g and were combined with untreated Mg wire (comparative example) or with ammonium phosphate-treated Mg wire. At one end of the produced cylindrical shaped body (Ø=10 mm, H=20 mm) a piece of a length of approx. 2 mm of the untreated or treated Mg wire protruded.

The produced wire cement composites were incubated in simulated body fluid (SBF) at 37° C. The SBF was buffered with TRIS and was exchanged 2× per week.

Figure 4:
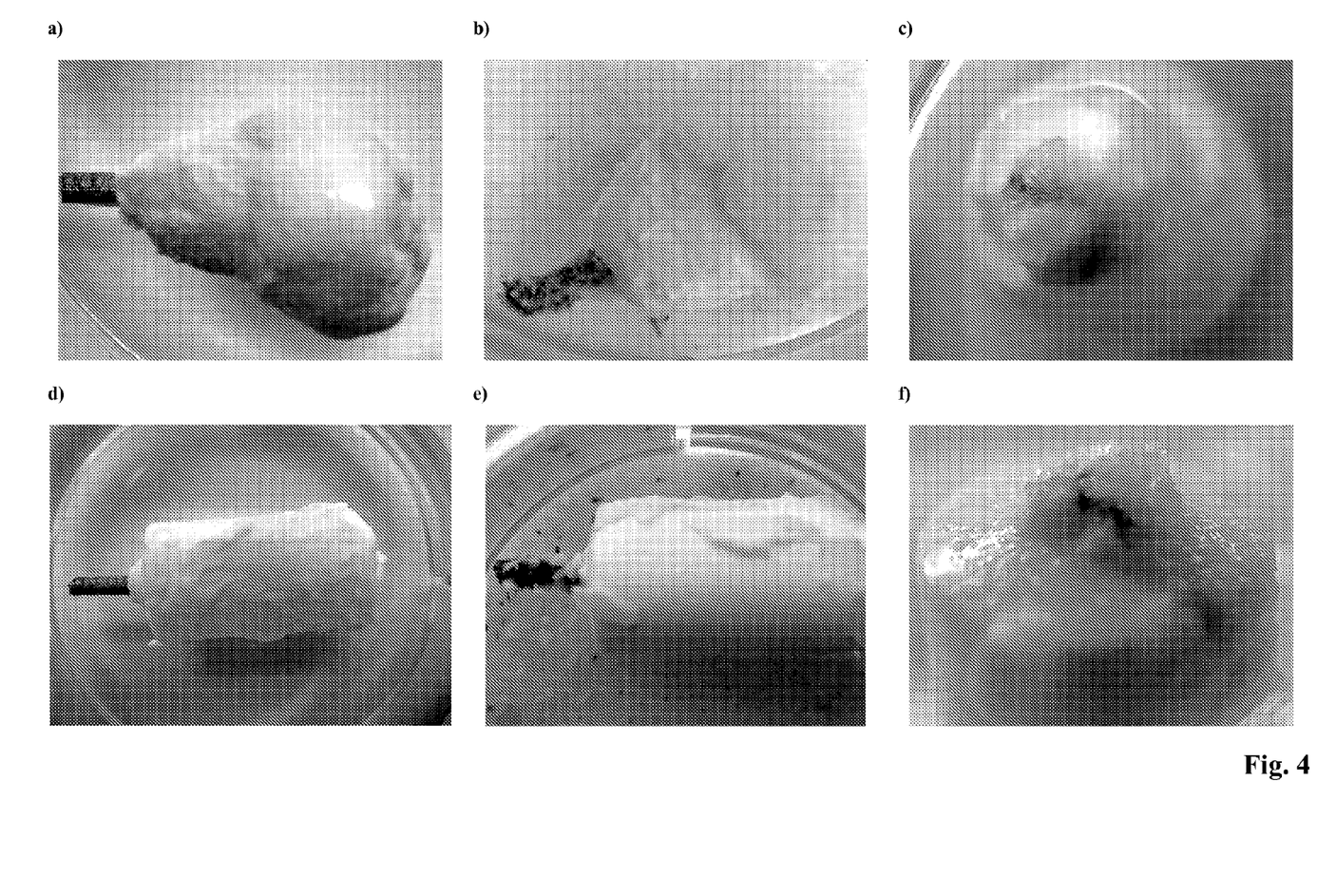
FIG. 4 Corrosion of an untreated magnesium wire in combination with calcium phosphate cement with ammonium phosphate (comparative example, a) 0 hours, b) 28 hours, c) 7 days) and of a magnesium wire treated with ammonium phosphates in combination with calcium phosphate cement with ammonium phosphate (d) 0 hours, e) 26 hours, f) 7 days) in simulated body fluid.

The corrosion behavior of both materials is shown in FIG. 4.

The free wire end of the untreated magnesium wire corroded already after 28 hours. The free wire end of the coated magnesium wire started to corrode significantly later.

Within one week, the exposed magnesium wire end that was treated with ammonium phosphate as well as the untreated exposed magnesium wire end clearly exhibit deposits of magnesium ammonium phosphate salt crystals which prevent a quick corrosion of the magnesium wire. The excess ammonium phosphates mixed with the cement dissolve partially due to storage in SBF and are available therefore for coating the free wire end. The salt deposits of magnesium ammonium phosphates can be seen especially well in the FIGS. 4c) and f). This shows clearly that the mineral bone cement which contains ammonium phosphates contributes to reducing the corrosion speed.

Embodiment 5: Composite Material of Calcium Phosphate Cement and Magnesium Chips Treated with Ammonium Phosphates Magnesium chips (Mg chips) of a size of 0.06-0.3 mm (Merck, Darmstadt) were stored at room temperature and afterwards incubated in 2.0 mol/l di-ammonium hydrogenphosphate solution for 2 hrs. with constant stirring.

Afterwards, the so treated Mg chips were separated, dried and added in 10, 20 and 30% by mass to calcium phosphate cement powder and mixed homogeneously.

Composite materials (cuboids, 6×6×12 mm) were produced from the resulting metal cement powder mixtures with 3 5 mol/l of di ammonium hydrogenphosphate solution in a ratio of 0.4 ml solution per 1 g of cement powder.

The produced composite materials were incubated in simulated body fluid (SBF) at 37° C. The SBF was buffered with TRIS and was exchanged 2× per week.

The compressive strength of the composite materials was determined in a universal testing machine (INSTRON) and summarized in Table 1. In this context, it is shown: (A) calcium phosphate cement, (B) calcium phosphate cement with 10% by weight of magnesium chips, (C) calcium phosphate cement with 20% by weight magnesium chips, and (D) calcium phosphate cement with 30% by weight of magnesium chips.

TABLE 1

Compressive strength [MPa] of CPC magnesium shaped bodies

| | Compressive Strengths [MPa] | | | |
|---|---|---|---|---|
| Time | (A) | (B) | (C) | (D) |
| 0 h | 24.26 +/− 5.10 | 25.12 +/− 6.72 | 21.98 +/− 6.03 | 30.29 +/− 3.23 |
| 2 weeks | 21.23 +/− 3.34 | 30.59 +/− 7.55 | 26.76 +/− 5.59 | 36.03 +/− 9.41 |

A slight strength increase of the shaped bodies which is due presumably to the formation of solid magnesium ammonium phosphate is to be noted after 2 weeks.

Embodiment 6: Composite Material of Magnesium Calcium Phosphate Cement and Magnesium Chips Treated with Ammonium Phosphate Magnesium chips (Mg chips) of a size of 0.06-0.3 mm, (Merck, Darmstadt) were stored at room temperature and afterwards incubated in 2.0 mol/l di-ammonium hydrogenphosphate solution for 2 hrs. with constant stirring.

Afterwards, the so treated Mg chips were separated, dried and added in 10, 20 and 30% by mass to magnesium calcium phosphate cement powder and mixed homogeneously.

Composite materials (cuboids, 6×6×12 mm) were prepared from the resulting metal cement powder mixtures with 3.5 mol/l ammonium phosphate solution (2 mol/l $(NH_4)_2HPO_4$+1.5 mol/l $(NH_4)H_2PO_4$) in a ratio of 0.4 ml solution per 1 g of cement powder.

The prepared composite materials were incubated in simulated body fluid (SU) at 37° C. The SBF was buffered with TRIS and was exchanged 2× per week.

The compressive strength of the composite materials was determined in a universal testing machine (INSTRON) and summarized in Table 2. In this context, it is shown: (A) magnesium calcium phosphate cement, (B) magnesium calcium phosphate cement with 10% by weight of magnesium chips, (C) magnesium calcium phosphate cement with 20% by weight of magnesium chips, and (D) magnesium calcium phosphate cement with 30% by weight of magnesium chips.

The shaped bodies made with ammonium phosphate solution with magnesium calcium phosphate cement powder remained shape-stable for several weeks.

Moreover, even a light strength increase can be observed after 2 weeks which is due presumably to the formation of solid magnesium ammonium phosphate in the shaped body.

TABLE 2

Compressive strengths [MPa] of MgCPC magnesium shaped bodies

| Time | Compressive Strengths [MPa] | | | |
|---|---|---|---|---|
| | (A) | (B) | (C) | (D) |
| 0 h | 69.99 +/− 6.83 | 79.33 +/− 13.23 | 82.53 +/− 3.91 | 82.88 +/− 15.05 |
| 2 weeks | 64.40 +/− 11.24 | 85.84 +/− 7.96 | 86.60 +/− 6.01 | 98.78 +/− 14.68 |

Embodiment 7: Composite Material from Calcium Phosphate Cement and Untreated Magnesium Chips Magnesium chips of a size of 0.06-0.3 mm (Merck, Darmstadt) were stored at room temperature. The magnesium chips were homogeneously mixed with calcium phosphate cement powder so that the proportion of the magnesium chips amounted to 30% by weight in the mixture.

Composite materials (cuboids, 6×6×12 mm) were prepared from the resulting metal cement powder mixtures with 3.5 mol/l of di-ammonium hydrogenphosphate solution in a ratio of 0.625 ml solution per 1 g of cement powder.

The prepared composite materials were incubated in simulated body fluid (SBF) at 37° C. After one week in SBF the prepared composite materials were stable and no gas formation was observed.

Embodiment 8: Composite Material from Magnesium Calcium Phosphate Cement and Untreated Magnesium Chips Magnesium chips of a size of 0.06-0.3 mm (Merck, Darmstadt) were stored at room temperature. The magnesium chips were mixed with magnesium calcium phosphate cement powder homogeneously so that the proportion of the magnesium chips amounted to 30% by weight in the mixture.

Composite materials (cuboids, 6×6×12 mm) were prepared from the resulting metal cement powder mixtures with 3.5 mol/l of di-ammonium hydrogenphosphate solution in a ratio of 0.625 ml solution per 1 g of cement powder.

The prepared composite materials were incubated in simulated body fluid (SBF) at 37° C. After one week in SBF the prepared composite materials were stable without gas formation.

Embodiment 9: Composite Material from Pasty Calcium Phosphate Cement and Magnesium Chips Treated with Ammonium Phosphates Magnesium chips of a size of 0.06~0.3 mm (Merck, Darmstadt) were stored at room temperature and afterwards incubated in 2.0 mol/l di-ammonium hydrogen phosphate solution for 2 hrs. with constant stirring. The so treated magnesium chips were separated from the solution and dried.

The treated chips were mixed homogenously with a pasty calcium phosphate cement (80% by weight of calcium phosphate cement powder in a medium-chain triglyceride (anhydrous carrier liquid) relative to the total mass of the paste, containing potassium hydrogenphosphate, cetyl phosphate and ethoxylated castor oil. The mass contents of the magnesium chips in the so made metal cement paste amounted to 10% by weight (relative to the total mass).

To the so made metal cement paste an aqueous solution was added whereby the setting reaction of the calcium phosphate cement is triggered. Composite materials (cuboids, 6×6×12 mm) were produced. In this context, 0.8 g of metal cement paste was mixed with 500 µl SBF. After 60 minutes of initial setting, the prepared composite materials were incubated in simulated body fluid (SBF) at 37° C. After one week in SBF the prepared composite materials were stable with out gas formation.

Embodiment 10: Composite Material from Pasty Calcium Phosphate Cement and Untreated Magnesium Chips Magnesium chips of a size of 0.06~0.3 mm (Merck, Darmstadt) Were stored at room temperature. The magnesium chips were mixed homogeneously with a pasty calcium phosphate cement (80% by weight of calcium phosphate cement powder in a medium-chain triglyceride (anhydrous carrier liquid) relative to the total mass of the paste, containing di-ammonium hydrogenphosphate, cetyl phosphate and ethoxylated castor oil. The mass contents of the magnesium chips in the so made metal cement paste amounted to 10% by weight (relative to the total mass).

To the so made metal cement paste an aqueous solution was added by which the setting reaction of the calcium phosphate cement is triggered. Composite materials (cuboids, 6×6×12 mm) were produced. In this context, 0.8 g of metal cement paste was mixed with 500 µl SBF. After 60 minutes of initial setting, the prepared composite materials were incubated in simulated body fluid (SBF) at 37° C. After one week in SBF the prepared composite materials were stable with gas formation.

What is claimed is:

1. A bone implant comprising a magnesium-containing metallic material and a mineral bone cement which contains water-soluble phosphate ion containing salts, wherein the magnesium-containing metallic material comprises a coating which contains magnesium ammonium phosphates.

2. The bone implant according to claim 1, wherein the layer containing ammonium phosphates has a thickness of more than 0.01 µm and less than 50 µm.

3. The bone gone implant according to claim 1, wherein, between the magnesium-containing metallic material and the layer of magnesium ammonium phosphates, a layer is provided which contains magnesium oxide and/or magnesium salts.

4. The bone implant according to claim 1, wherein the mineral bone cement contains ammonium ion containing and phosphate ion containing salts.

5. The bone implant according to claim 4, wherein the ammonium phosphates are selected from the group consisting of $(NH_4)_3PO_4$, $(NH_4)_2HPO_4$, $(NH_4)H_2PO_4$, ammonium salts of the dimeric, oligomeric and polymeric phosphoric acid and of partially substituted phosphoric acid, and mixtures thereof.

6. The bone implant according to claim 1, wherein the mineral bone cement contains calcium phosphates and/or magnesium phosphates.

7. The bone implant according to claim 1, wherein the magnesium-containing metallic material is present in the form of fibers, threads, filaments, wires, wires or threads processed to woven fabrics, braided fabrics, knit fabrics, knitted materials, fleeces, nonwovens, membranes or cords web materials obtainable from fibers, threads, filaments or wires, perforated sheet metal or expanded metal or shaped bodies that are formed from perforated sheet metal or expanded metal, or an open-cell metal foam.

8. A kit for producing a bone implant, comprising d) a bone cement preparation comprising mineral bone cement powder and water-soluble phosphate ion containing salts, and e) a magnesium-containing metallic material with a magnesium oxide layer and/or a magnesium salt layer and ammonium ion containing and phosphate ion containing salts, or f) a magnesium-containing metallic material with a coating containing magnesium ammonium phosphates and optionally ammonium ion containing and phosphate ion containing salts.

9. The kit according to claim 8, wherein the bone cement preparation is present in the form of an anhydrous paste which contains mineral bone cement powder dispersed in an anhydrous carrier liquid.

10. The kit according to claim 8, wherein ammonium ion containing and phosphate ion containing salts are contained as solids or are present in the form of an aqueous solution as a component that is packaged separate from the bone cement preparation of the kit.

11. The kit according to claim 8, wherein the ammonium ion containing and phosphate ion containing salts are present as a coating on the magnesium-containing metallic material.

12. The kit according to claim 8, wherein the mineral bone cement contains calcium phosphates and/or magnesium phosphates.

13. The kit according to claim 8, wherein the mineral bone cement and the magnesium-containing metallic material are present as a component of the kit that is contacted with an aqueous solution for producing a solid composite material.

14. The kit according to claim 8, wherein the mineral bone cement is configured as a two-component system which contains an anhydrous component with mineral bone cement powder and a water-containing component.

15. The kit according to claims 8, wherein the mineral bone cement contains ammonium ion containing and phosphate ion containing salts, selected from the croup consisting of $(NH_4)_3PO_4$, $(NH_4)_2HPO_4$, $(NH_4)H_2PO_4$, ammonium salts of the dimeric, oligomeric and polymeric phosphoric acid and partially substituted phosphoric acid, and mixtures thereof.

16. A bone implant produced with a kit according to claim 8.

* * * * *